United States Patent
Cathier

(10) Patent No.: US 7,355,605 B2
(45) Date of Patent: Apr. 8, 2008

(54) METHOD AND SYSTEM FOR AUTOMATIC ORIENTATION OF LOCAL VISUALIZATION TECHNIQUES FOR VESSEL STRUCTURES

(75) Inventor: Pascal Cathier, Exton, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 379 days.

(21) Appl. No.: 10/945,022

(22) Filed: Sep. 20, 2004

(65) Prior Publication Data

US 2005/0105829 A1    May 19, 2005

Related U.S. Application Data

(60) Provisional application No. 60/504,910, filed on Sep. 22, 2003.

(51) Int. Cl.
*G09G 5/02* (2006.01)
(52) U.S. Cl. ............ 345/589; 345/419; 382/128; 382/131; 382/296
(58) Field of Classification Search ............ 382/128, 382/296, 131; 345/419, 589
See application file for complete search history.

(56) References Cited

U.S. PATENT DOCUMENTS 6,609,021 B1   8/2003   Fan et al.
6,690,816 B2 *   2/2004   Aylward et al. ............ 382/128

OTHER PUBLICATIONS

Krissian K., et al., "Multiscale Segmentation of the Aorta in 3D Ultrasound Images," Proceedings of the 25th Annual International Conference of the IEEE EMBS 2003.
Haussbecker Horst et al., "A Tensor Approach for Local Structure Analysis in Multi-Dimensional Images" XP-002311193.
Van Vliet, Lucas J. et al., "Estimators for Orientation and Anisotropy in digitized Images," Proceedings of the First Conference of the Advanced School for Computing and Imaging pp. 442-450 1995.
Knutsson Hans, "Representing Local Structure Using Tensors," XP-002311194.
International Search Report.

* cited by examiner

*Primary Examiner*—Kimbinh T. Nguyen

(57) ABSTRACT

A method of orienting a tubular structure in a digital image is provided, wherein the image comprises a plurality of intensities corresponding to a domain of points in a D-dimensional space. The method includes selecting a point in the domain of the image, computing, in a neighborhood of the selected point, a gradient of the image, computing an elementary structure tensor at the selected point, determining a structure tensor for the selected point, and finding the eigenvalues of the structure tensors. The eigenvector corresponding to the smallest eigenvalue is aligned with the tubular structure. A cartwheel projection can be calculated about an axis defined by the eigenvector that is aligned with the tubular structure.

16 Claims, 4 Drawing Sheets

METHOD AND SYSTEM FOR AUTOMATIC ORIENTATION OF LOCAL VISUALIZATION TECHNIQUES FOR VESSEL STRUCTURES

CROSS REFERENCE TO RELATED UNITED STATES APPLICATIONS

This application claims priority from "Automatic orientation of local visualization techniques for vessel structures", U.S. Provisional Application No. 60/504,910 of Pascal Cathier, filed Sep. 22, 2003, the contents of which are incorporated herein by reference.

TECHNICAL FIELD AND BACKGROUND

This invention is directed to recognizing vascular structures in a digital medical image.

The diagnostically superior information available from data acquired from current imaging systems enables the detection of potential problems at earlier and more treatable stages. Given the vast quantity of detailed data acquirable from imaging systems, various algorithms must be developed to efficiently and accurately process image data. With the aid of computers, advances in image processing are generally performed on digital or digitized images.

Digital images are created from an array of numerical values representing a property (such as a grey scale value or magnetic field strength) associable with an anatomical location points referenced by a particular array location. The set of anatomical location points comprises the domain of the image. In 2-D digital images, or slice sections, the discrete array locations are termed pixels. Three-dimensional digital images can be constructed from stacked slice sections through various construction techniques known in the art. The 3-D images are made up of discrete volume elements, also referred to as voxels, composed of pixels from the 2-D images. The pixel or voxel properties can be processed to ascertain various properties about the anatomy of a patient associated with such pixels or voxels. Computer-aided diagnosis ("CAD") systems play a critical role in the analysis and visualization of digital imaging data.

An important application of computed tomographic (CT) imaging systems, as well as magnetic resonance (MR) imaging and 3-D x-ray (XR) imaging systems, is to produce 3D image data sets for vascular analysis, which can include analysis of a variety of tortuous tubular structures such as airways, ducts, nerves, blood vessels, etc. Production of such 3D image data sets is particularly important for radiologists, who are called upon to provide thorough visual reports to allow assessments of stenosis or aneurysm parameters, quantify lengths, section sizes, angles, and related parameters. Information concerning, for example, the most acute stenosis on a selected vessel section, the largest aneurysm on a selected vessel section, or the tortuosity of a vessel, is commonly utilized by physicians to allow for surgical planning. For productivity reasons, as well as to reduce film costs, the 3D image data sets should be limited to only a small set of significant images.

To facilitate the obtaining of useful information for vascular analysis in an efficient manner, conventional medical imaging systems sometimes provide 3D visualization software. Such software is provided either on the imaging systems themselves or on analysis workstations, and provides a set of tools to perform length, angle or volume measurements and to visualize a volume in different ways, for example, using cross-sections, navigator or volume rendering. With respect to vascular analysis, in particular, the software can be used to obtain multiple oblique slices of a particular vessel to allow for analysis of the vessel.

Analyzing tortuous structures, such as airways, vessels, ducts or nerves is one of the major applications of medical imaging systems. This task is accomplished today by using multiple oblique slices to analyze local segments of these structures. These views provide a clear, undistorted picture of short sections from these objects but rarely encompass their full length. Curved reformation images provide synthetic views that capture the whole length of these tubular objects and are therefore well suited to this analysis task. True 3D length measurements along the axis can be obtained from these views and they are not too far from the real anatomy in many cases. Curved reformation images can be generated by sampling values along a curve at equidistant points to generate lines, and then translating this curve by a sampling vector to generate the next image line.

Therefore, it would be advantageous if new methods and apparatuses were developed for allowing medical imaging systems and related 3D visualization software to produce useful 3D imaging data sets in a more efficient, consistent, repeatable, rapid, and less operator-dependent manner. It would particularly be advantageous if such new methods and apparatuses facilitated vascular analysis, including the analysis and imaging of tubular vessels and related stenoses, aneurysms, and tortuosity. It further would be advantageous if such methods and apparatuses could be employed both during imaging and in post-processing after imaging is completed.

SUMMARY OF THE INVENTION

In one aspect of the invention, a method of orienting a tubular structure in a digital image, wherein the image comprises a plurality of intensities corresponding to a domain of points in a D-dimensional space, is provided. The method includes selecting a point in the domain of the image, computing, in a neighborhood of the selected point, a gradient of the image, computing an elementary structure tensor at the selected point, determining a structure tensor for the selected point, finding the eigenvalues of the structure tensors, and analyzing the eigenvalues to find an eigenvector aligned with the tubular structure.

In a further aspect of the invention, the gradient of the image is estimated by convolving the image with a derivative of a Gaussian kernel G over the neighborhood centered about the selected point.

In a further aspect of the invention, the Gaussian kernel has a standard deviation $\sigma_G$, wherein $\sigma_G$ is about 2 orders of magnitude smaller than the size of the image.

In a further aspect of the invention, the elementary structure tensor can be defined by multiplying the gradient of an image with its transpose.

In a further aspect of the invention, the structure tensor can be determined by convolving the elementary structure tensor with a Gaussian kernel of standard deviation $\sigma_T$, wherein $\sigma_T$ corresponds to the size of the object being sought.

In a further aspect of the invention, the eigenvalues can be found by performing a Householder QL decomposition.

In a further aspect of the invention, the eigenvector corresponding to the smallest eigenvalue is aligned with the tubular structure.

In a further aspect of the invention, the neighborhood of the selected point can be compared to a vascular structure by comparing the two smallest eigenvalues of the neighborhood, wherein the two smallest eigenvalues are dissimilar if the neighborhood is locally similar to a vascular structure.

In a further aspect of the invention, a cartwheel projection can be calculated about an axis defined by the eigenvector that is aligned with the tubular structure.

BRIEF DESCRIPTION OF THE DRAWINGS

FIG. 5 depicts an exemplary computer system for implementing a preferred embodiment of the invention.

DETAILED DESCRIPTION OF THE PREFERRED EMBODIMENT

Figure 1:
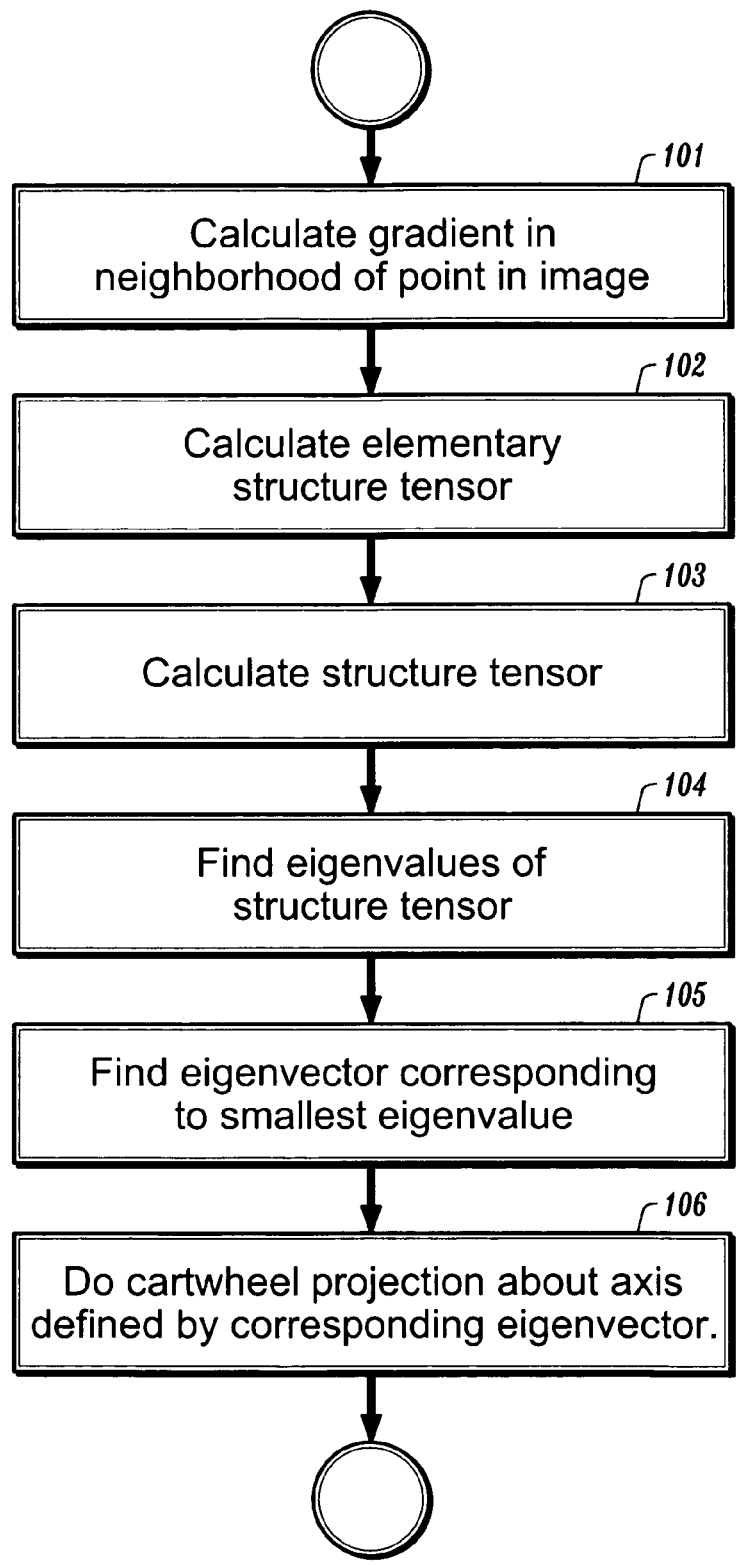
FIG. 1 depicts a flow chart of a preferred method of the invention.

The present invention is directed to CAD methods for automatically detecting a vessel axis of a vascular structure and using the axis to aid in the visualization of such structures.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, the methods of the inventions are not limited to such images, and can be applied to images of any dimension, e.g. a 2-D picture or a 3-D volume. The present invention is preferably performed on a computer system, such as a Pentium®-class personal computer, running computer software that implements the algorithm of the present invention. The computer includes a processor, a memory and various input/output means. A series of digital images representative of a thoracic volume are input to the computer. The terms "digital" and "digitized" as used herein will refer to images or volumes, as appropriate, in a digital or digitized format acquired via a digital acquisition system or via conversion from an analog image.

Vascular structures are examples of tubular-shaped objects, which are commonly found in medical images. Other examples of tubular objects in medical images can include vessels, bronchi, bowels, ducts, nerves and specific bones. Representation and analysis of tubular objects in medical images can aid medical personnel in understanding the complex anatomy of a patient and facilitate medical treatments. When reviewing 3D images of vascular structures such as CT scans, a physician can use axial slices to detect any abnormal structures (e.g. nodules or emboli), but to further analyze the shape of the structure, additional views are useful. One possibility is the cartwheel projection, where the projection plane is turned around an axis. It makes it easier for a physician to assess whether a structure is round or not. Another possibility is to analyze projection planes orthogonal to the vessel axis. These techniques require an axis as an input. This axis should preferably be the axis of the vessel. Taking an arbitrary axis by default can sometimes yield bad visualization results.

In a typical analysis situation, a physician reviews a volumetric image, such as a CT image of the lungs, looking for spherical structures. The images are huge in all three dimensions. Usually the physician only looks at axial images, i.e. X-Y slices of the volume, one at a time, usually starting from the head down, and back. The slices are typically 512×512 pixels, while the structures the physician is looking at are typically a few pixels wide. So, while the physician can easily dismiss most of the image, sometimes he or she may want to have a closer look at a structure. What's more, when having a closer look, he or she may want to have full 3D information, instead of just the X-Y cut. In this case, the cartwheel projection is useful, along with other 3D tools that can be used either by themselves or together with the cartwheel projection.

The cartwheel projection can be used to differentiate between spherical and tubular structures. The problem is that, using only X-Y slices, both kinds of structures can appear as circles. Now, having a full 3-D rotation enables the physician to differentiate between vessels and nodules. The cartwheel projection can perform that differentiation quite well, but in its original form, the rotation axis of the cartwheel is fixed (typically the X or Y axis) and is thus random with respect to the vessel axis. Therefore, the physician has to search for the rotation angle of the cartwheel for which the cartwheel plane contains the vessel axis, in order to be able to differentiate between a vessel and a nodule. The methods disclosed herein are directed to aiding the detection of a vessel axis and using it in an appropriate way in these visualization techniques.

In a preferred embodiment of the invention, a local structure tensor can be used to locate the main axis of a vascular object, starting from an estimated local principle axis. An initial estimate of the location of the principle axis can be made by a user using an input device such as a mouse to select a point in a slice. Referring now to FIG. 1, a preferred method for calculating a structure tensor starts by calculating the gradient of an image, which is a 3D vector formed of the image partial derivatives along the canonical axes:

$$\nabla I = \left[\frac{\partial I}{\partial x}, \frac{\partial I}{\partial y}, \frac{\partial I}{\partial z}\right]^T$$

In practice, an image is only sampled at discrete points, and is subject to noise. In a preferred embodiment, at step 101, a gradient in a neighborhood of an image can be estimated at each point in the neighborhood by convolving the image with a Gaussian derivative:

$$\frac{\partial I}{\partial x} \approx \frac{\partial G}{\partial x} * I,$$

where G is a discrete normalized, D-dimensional Gaussian kernel of standard deviation $\sigma_G$, $$G(x) = \frac{1}{\left(\sqrt{2\pi}\,\sigma_G\right)^D} \exp\left(-\frac{x^2}{2\sigma_G^2}\right),$$

and the operator * is a convolution. The standard deviation is typically rather small as compared to the overall size of the image, e.g. 3 voxels maximum, or two orders of magnitude smaller than the number of voxels in one dimension of the image, and is selected to limit the computation of the gradient to a small volume about the selected point and to smooth out the effects of noise.

The Structure Tensor is a 3×3 matrix that can be derived by convolving at step 103 the outer product of the gradient with its transpose with a spatial filter whose size corresponds to an object being sought. A preferred spatial filter is a Gaussian kernel:

$$T = G_\sigma * \nabla I . \nabla I^T.$$

Here, sigma can be quite big and is loosely related to the size of the object sought. Other convolution kernels could be used, but the Gaussian kernel is the preferred one. The 3 eigenvalues of the Structure Tensor can be computed at step 104 by any suitable technique known in the art. One such technique is the Householder QL decomposition.

The eigenvectors of the structure tensor are all mutually orthogonal, and, at step 105, the eigenvector corresponding to the smallest eigenvalue is most likely to be the axis of a vascular structure. Indeed, when a starting point inside or even near a vessel is chosen, one of the eigenvectors, the one with the smallest eigenvalue, will most likely be aligned with the vessel. Even in a situation where a vessel is bent or branches into separate parts, examination of the eigenvector associated with the smallest eigenvalue will at least be locally aligned with the vessel. For example, eigenvalues can be used to check if the image is locally similar to a vascular structure by comparing the two smallest eigenvalues, which should be very dissimilar in the normal case.

Figure 2:
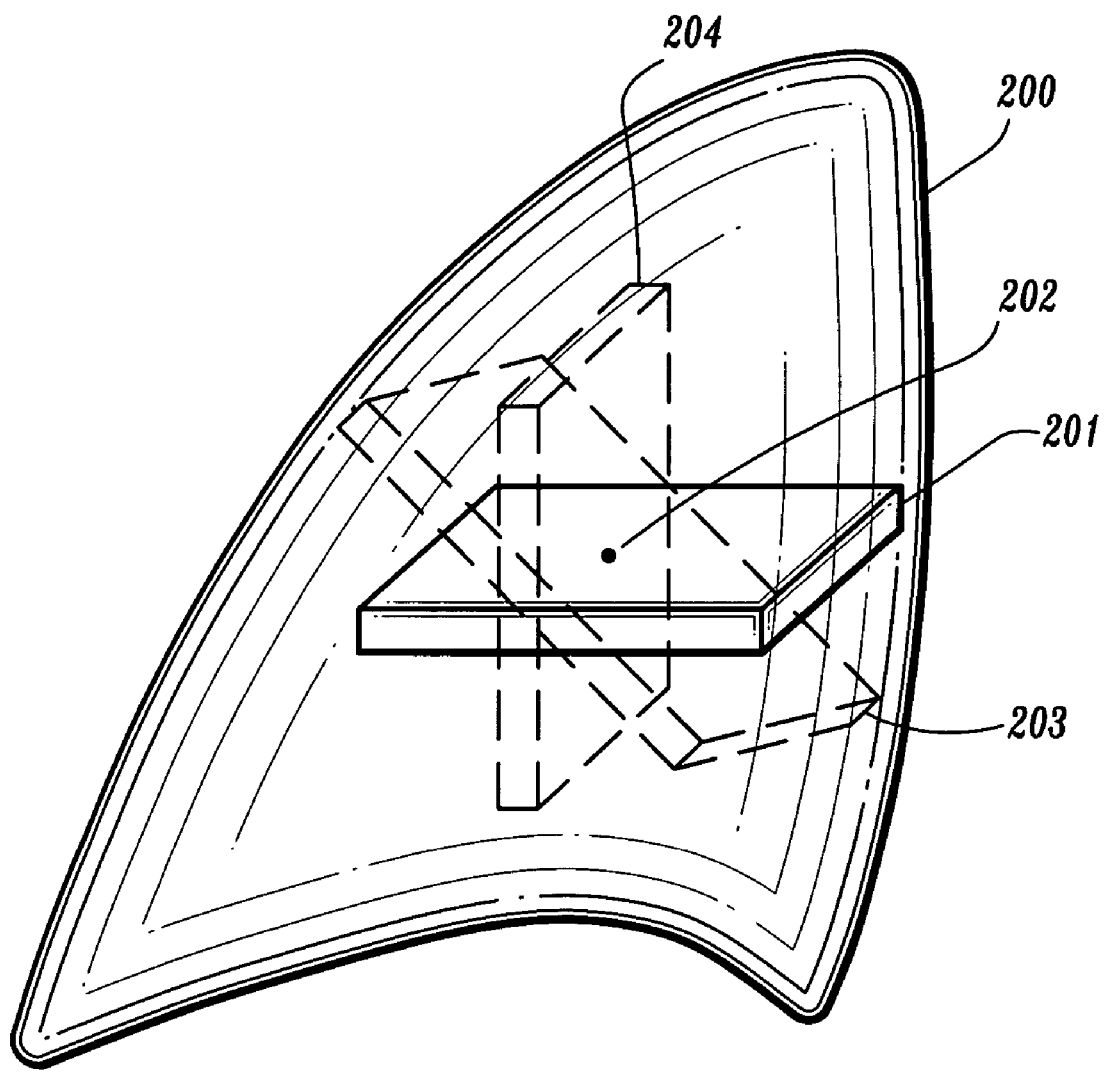
FIG. 2 is a diagram illustrating a cartwheel projection of an image slice centered at an object of interest.

The cartwheel projection can be performed at step 106 around this axis defined by the click-point and this eigenvector. FIG. 2 illustrates a cartwheel projection of an object of interest. Each axial image slice that is put through the cartwheel projection is obtained from an image scan of a lung 200 using a CT device, and is centered at an object of interest, such as a suspicious structure. As depicted in FIG. 2, a spinning projection plane 201 is rotated 180 degrees, around a point of interest 202, and a series of 2D projections of the axial image slice (hereafter called cartwheel projection image slices) such as cartwheel projection image slices 203 and 204, are obtained. The rotation angles can be set at predefined intervals, such as, for example, every 5 degrees, in which case 36 individual cartwheel projection image slices would be generated for each input object of interest on a given axial image slice. Likewise, if the interval had been set to 1 degree, 180 individual cartwheel projection image slices would be generated for each input object of interest.

The cartwheel projection can be used to differentiate between spherical and tubular structures. Projections orthogonal to the axis can also be computed, to have slices that cut orthogonal to the vessel. Once the rotation axis is aligned with the vessel, it is obvious from a cartwheel projection that the structure is a vessel, because from the first angle to the last, all projection planes cut the vessel right through its axis.

Figure 3:
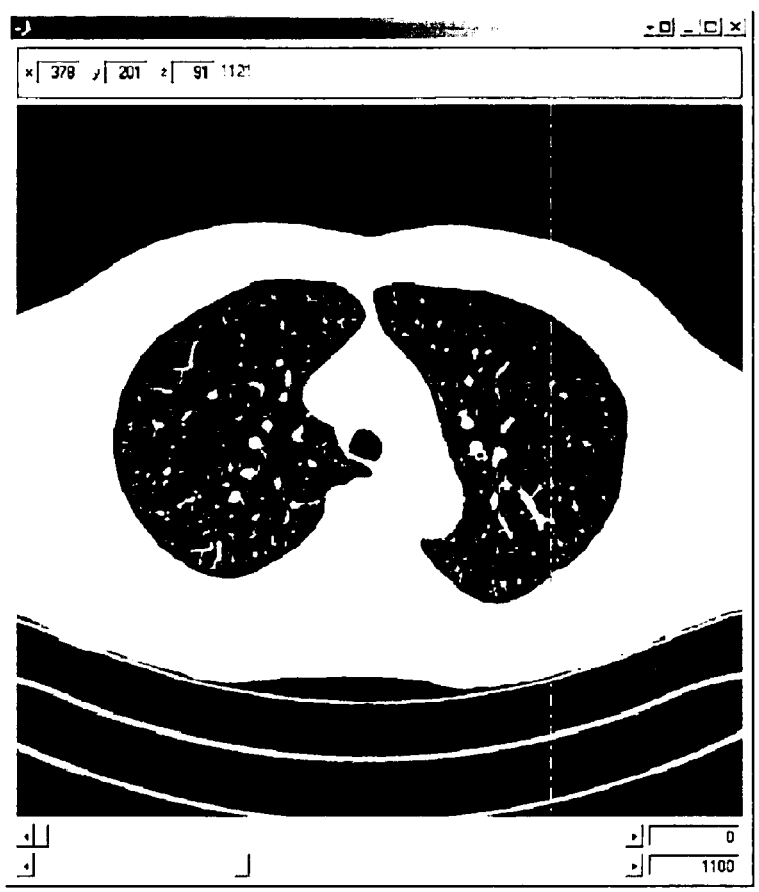
FIG. 3 depicts a user selecting a structure to analyze.
Figure 4:
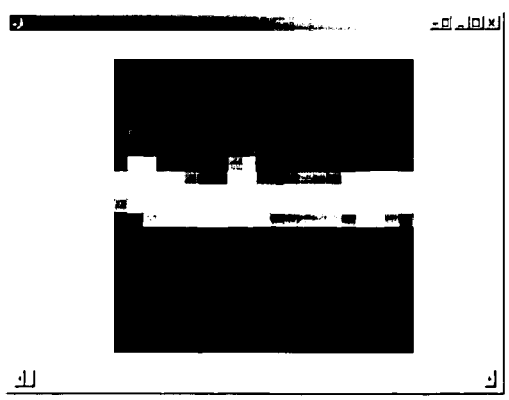
Figure 5:
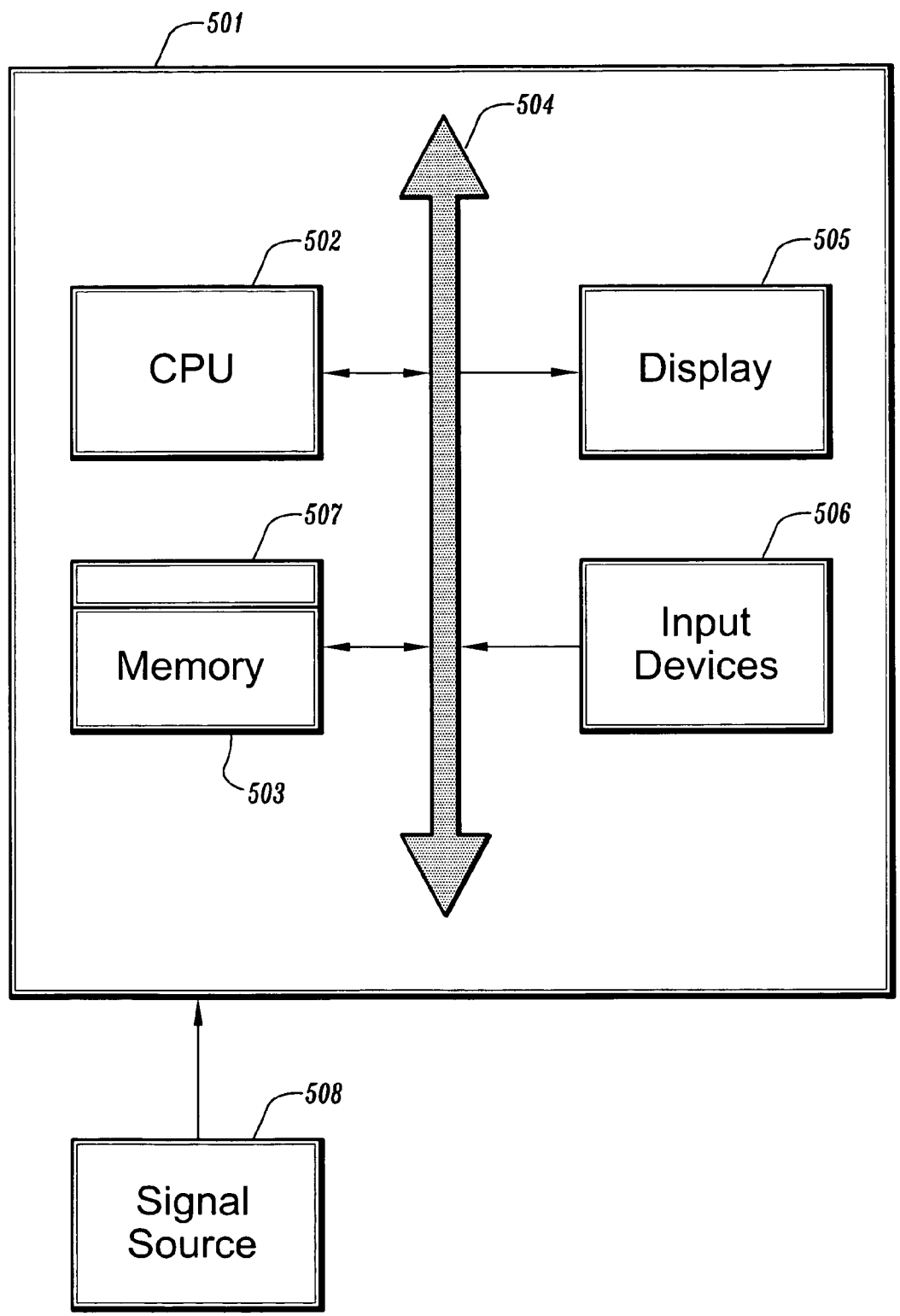
FIG. 5 depicts a vessel found by a method of the invention.

FIGS. 3 and 4 illustrate an example of such an interface. In FIG. 3, a user clicks in the image where he or she wants a local view, as indicated by the crosshair in the figure. If the structure under the mouse point is a vessel, the cartwheel projection is done along its axis, which is displayed automatically in a given direction. FIG. 4 illustrates a horizontally displayed vessel.

If a structure is a nodule, the rotation axis can become more or less random, since all cuts will yield a disc anyway. However, in this situation, the physician would usually prefer to have a non-random axis, typically the X or Y axis. So when computing the structure tensor, if one detects that all eigenvalues are close to each other, one can shift from using the tensor axis to using the standard cartwheel axis.

It is to be understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Referring now to FIG. 4, according to an embodiment of the present invention, a computer system 401 for implementing the present invention can comprise, inter alia, a central processing unit (CPU) 402, a memory 403 and an input/output (I/O) interface 404. The computer system 401 is generally coupled through the I/O interface 404 to a display 405 and various input devices 406 such as a mouse and a keyboard. The support circuits can include circuits such as cache, power supplies, clock circuits, and a communication bus. The memory 403 can include random access memory (RAM), read only memory (ROM), disk drive, tape drive, etc., or a combinations thereof. The present invention can be implemented as a routine 407 that is stored in memory 403 and executed by the CPU 402 to process the signal from the signal source 408. As such, the computer system 401 is a general purpose computer system that becomes a specific purpose computer system when executing the routine 407 of the present invention.

The computer system 401 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method of orienting a tubular structure in a digital medical image, wherein said image comprises a plurality of intensities corresponding to a domain of points in a D-dimensional space, said method comprising the steps of:
   selecting a point in the domain of the image;
   computing, in a neighborhood of said selected point, a gradient of the image;
   determining a structure tensor for said selected point;
   finding eigenvalues of the structure tensors;
   analyzing said eigenvalues to find an eigenvector aligned with said tubular structure; and
   comparing said neighborhood of said selected point to a vascular structure by comparing the two smallest eigenvalues of said neighborhood, wherein said two smallest eigenvalues are dissimilar if said neighborhood is locally similar to a vascular structure.

2. The method of claim 1, wherein the gradient of the image is estimated by convolving the image with a derivative of a Gaussian kernel G over said neighborhood centered about said selected point.

3. The method of claim 2, wherein said Gaussian kernel has a standard deviation $\sigma_G$, wherein $\sigma_G$ is two orders of magnitude smaller than the size of the image.

4. The method of claim 1, wherein the structure tensor can be determined by convolving the outer product of the gradient with its transpose with a Gaussian kernel of standard deviation $\sigma_T$, wherein $\sigma_T$ corresponds to the size of the object being sought.

5. The method of claim 1, wherein the eigenvalues are found by performing a Householder QL decomposition.

6. The method of claim 1, wherein the eigenvector that is aligned with the tubular structure corresponds to the smallest eigenvalue.

7. The method of claim 1, further comprising calculating a cartwheel projection about an axis defined by the eigenvector that is aligned with said tubular structure.

8. A method of orienting a tubular structure in a digital medical image, wherein said image comprises a plurality of intensities corresponding to a domain of points in a D-dimensional space, said method comprising the steps of:
   selecting a point in the domain of the image;
   computing, in a neighborhood of said selected point, a gradient of the image by convolving the image with a derivative of a Gaussian kernel G over of standard deviation $\sigma_G$, wherein $\sigma_G$ is two orders of magnitude smaller relative to the size of the image;
   determining a structure tensor for said selected point by convolving the outer product of the gradient with its transpose with a Gaussian kernel of standard deviation $\sigma_T$, wherein $\sigma_T$ corresponds to the size of the object being sought;
   finding the eigenvalues of the structure tensors by performing a Householder QL decomposition;
   finding a smallest eigenvalue of said eigenvalues to find a corresponding eigenvector, wherein said corresponding eigenvector is aligned with said tubular structure; and
   calculating a cartwheel projection about an axis defined by the eigenvector that is aligned with said tubular structure.

9. The method of claim 8, further comprising comparing said neighborhood of said selected point to a vascular structure by comparing the two smallest eigenvalues of said neighborhood, wherein said two smallest eigenvalues are dissimilar if said neighborhood is locally similar to a vascular structure.

10. A program storage device readable by a computer, tangibly embodying a program of instructions executable by the computer to perform the method steps for orienting a tubular structure in a digital medical image, wherein said image comprises a plurality of intensities corresponding to a domain of points in a D-dimensional space, said method comprising the steps of:
   selecting a point in the domain of the image;
   computing, in a neighborhood of said selected point, a gradient of the image;
   computing an elementary structure tensor at said selected point;
   determining a structure tensor for said selected point;
   finding eigenvalues of the structure tensors; and
   analyzing said eigenvalues to find an eigenvector aligned with said tubular structure.

11. The computer readable program storage device of claim 10, the method steps further comprising estimating the gradient by convolving the image with a derivative of a Gaussian kernel G of standard deviation $\sigma_G$ centered about said selected point, wherein $\sigma_G$ is two orders of magnitude smaller relative to the size of the image.

12. The computer readable program storage device of claim 10, the method steps further comprising determining the structure tensor by convolving the outer product of the gradient with its transpose with a Gaussian kernel of standard deviation $\sigma_T$, wherein $\sigma_T$ corresponds to the size of the object being sought.

13. The computer readable program storage device of claim 10, the method steps further comprising performing a Householder QL decomposition to find the eigenvalues of the structure tensor.

14. The computer readable program storage device of claim 10, the method steps further comprising finding the eigenvector corresponding to the smallest eigenvalue, wherein said corresponding eigenvector is aligned with said tubular structure.

15. The computer readable program storage device of claim 10, the method steps further comprising comparing said neighborhood of said selected point to a vascular structure by comparing the two smallest eigenvalues of said neighborhood, wherein said two smallest eigenvalues are dissimilar if said neighborhood is locally similar to a vascular structure.

16. The computer readable program storage device of claim 10, the method steps further comprising calculating a cartwheel projection about an axis defined by the eigenvector that is aligned with said tubular structure.

* * * * *